(12) United States Patent
Leong et al.

(10) Patent No.: US 9,632,075 B2
(45) Date of Patent: Apr. 25, 2017

(54) PREVENTION OR ATTENUATION OF NEUROPATHIC PAIN BY BILE ACIDS

(71) Applicant: Metselex, Inc., Minneapolis, MN (US)

(72) Inventors: Mai Lan Leong, Minneapolis, MN (US); Clifford Steer, Eagan, MN (US); Martin Wessendorf, St. Paul, MN (US)

(73) Assignee: Meselex, Inc., Minneapolis, MN (US)

( * ) Notice: Subject to any disclaimer, the term of this patent is extended or adjusted under 35 U.S.C. 154(b) by 0 days.

(21) Appl. No.: 14/355,759

(22) PCT Filed: Nov. 1, 2012

(86) PCT No.: PCT/US2012/062927
§ 371 (c)(1),
(2) Date: May 1, 2014

(87) PCT Pub. No.: WO2013/067096
PCT Pub. Date: May 10, 2013

(65) Prior Publication Data
US 2014/0296194 A1    Oct. 2, 2014

Related U.S. Application Data

(60) Provisional application No. 61/554,463, filed on Nov. 1, 2011.

(51) Int. Cl.
*A61K 31/575* (2006.01)
*A61K 31/573* (2006.01)
*G01N 33/50* (2006.01)
*A61B 5/00* (2006.01)

(52) U.S. Cl.
CPC ....... *G01N 33/5058* (2013.01); *A61B 5/4827* (2013.01); *A61K 31/573* (2013.01); *A61K 31/575* (2013.01)

(58) Field of Classification Search
CPC ............................. A61K 31/575; A61K 31/573

USPC .................................................... 514/70, 182
See application file for complete search history.

(56) References Cited

U.S. PATENT DOCUMENTS 7,884,069 B2 * 2/2011 Schaebitz ............ A61K 38/193
424/85.1

OTHER PUBLICATIONS

Colak et al. Tauroursodeoxycholic acid and secondary damage after spinal cord injury in rats. Journal of Clinical Neuroscience 15 (2008) pp. 665-671.*
Marinelli et al. Rostral ventromedial medulla neurons that project to the spinal cord express multiple opioid receptor phenotypes. The Journal of Neuroscience, Dec. 15, 2002, 22(24): 10847-10855.*

* cited by examiner

*Primary Examiner* — Jennifer M Kim
(74) *Attorney, Agent, or Firm* — Schwegman Lundberg & Woessner, P.A.

(57) ABSTRACT

Methods of reducing or abolishing neuropathic pain in humans and animals are discussed. In some examples administration of the apoptosis inhibitor tauroursodeoxycholic acid (TUDCA), greatly reduced both neuronal loss and the increase in glia, and partially reversed spinal nerve ligation (SNL)-induced mechanical hypersensitivity. Among RVM neurons, serotonergic (5-HT) neurons decreased by 35% ipsilateral to SNL. In some examples, the density of 5-HT immunoreactive varicosities in the superficial dorsal horn of the spinal cord was lower ipsilateral to SNL. The RVM 5-HT neurons that remained after SNL appeared to facilitate nociception. When rats that had undergone SNL were treated with the 5-HT neurotoxin, 5,7-dihydroxytryptamine (5,7-DHT), mechanical withdrawal thresholds increased significantly. In some examples nerve injury induces death of antinociceptive RVM neurons which can be reduced or abolished by TUDCA. In some examples, that the loss of RVM neurons shifts the balance of descending control from pain inhibition to pain facilitation.

8 Claims, 10 Drawing Sheets

PREVENTION OR ATTENUATION OF NEUROPATHIC PAIN BY BILE ACIDS

BACKGROUND OF THE INVENTION

Neuropathic Pain:

Trauma or disease affecting peripheral nerves frequently results in the development of chronic, sometimes intractable, neuropathic pain. Existing treatments for neuropathic pain have limited effectiveness and produce relatively frequent adverse effects. Studies have shown that enhanced pain induced by peripheral nerve injury is associated with increased spontaneous and evoked discharges from injured and/or adjacent nerves. Although this increased afferent discharge is vital in establishing spinal sensitization in the period immediately following nerve injury, the time course of such abnormal afferent activity is inconsistent with the long duration of heightened pain.

Existing treatments for the amelioration of neuropathic pain include both drugs and surgery. Depending upon the specific type of neuropathic pain, drug treatments may range from non-steroidal anti-inflammatory drugs (NSAIDS), to anti-depressants, to agonists and antagonists of neurotransmitters (e.g., glutamate and GABA) to opiate analgesics. These treatments can be effective in some cases (with their efficacy varying from patient to patient) but suffer from side-effects, including toxicity, motor impairment, tolerance, and abuse potential. Moreover, although they can reduce the pain sensations, they seldom result in complete alleviation of the pain. Surgical treatments are typically limited to attempts to relieve pressure on nerve trunks (e.g., in cases of pain from herniated disks or carpel tunnel syndrome) and in these cases they sometimes can be completely effective. However, surgery is much less useful in cases of frank nerve damage, e.g., from accidental or surgical injury to a nerve.

SUMMARY OF THE INVENTION

Previous work has suggested that the pathology of neuropathic pain is due in part to death of neurons in the CNS and/or dorsal root ganglia. Work by the inventors has revealed that neuropathic pain may be due in part to death of antinociceptive rostral ventromedial (RVM) neurons, leading to decreased descending inhibition of nociception. Subsequent to the cell loss, gliosis occurs, which may also play a role in neuropathic pain. The inventors have discovered that the apotosis (programmed cell death) inhibitor tauroursodeoxycholic acid (TUDCA) significantly reduced both neural loss and the increase in glia, and partially reversed spinal nerve ligation (SNL)-induced mechanical hypersensitivity. Among the RVM neurons, the inventors discovered that serotonergic (5-HT) neurons decreased significantly ipsilateral to SNL. Further, the density of 5-HT-immunoreactive varicosities in the superficial dorsal horn of the spinal cord was lowered.

DETAILED DESCRIPTION OF THE INVENTION

It has been shown that nerve injury and disease can trigger a range of responses in both the peripheral and central nervous systems that contribute to chronic neuropathic pain. In the periphery, injured primary sensory neurons develop hyperexcitability and abnormal impulse generation. Other pathophysiological changes observed in injured primary sensory neurons include the altered regulation and expression of certain molecules (e.g. neuropeptides, ion channels, enzymes, etc.). Increased spinal cord excitability ipsilateral to the injury (i.e. central sensitization) also appears to contribute crucially to abnormal pain conditions after tissue injury. N-methyl-D-aspartate (NMDA) receptor activation is one of the principal mechanisms in central sensitization, and its role in neuropathic pain is implied by preclinical studies showing that NMDA 20 receptor antagonists are effective in alleviating experimental neuropathic pain. Pathophysiological changes in the RVM also contribute to neuropathic pain. Microinjection of a NMDA receptor antagonist before, and microinjection of lidocaine in the RVM after SNL have both been shown to reduce allodynia, suggesting that activation of (and activity in) the RVM contributes to cutaneous hypersensitivity. Consistent with this idea, lesioning the DLF, in which RVM axons descend to the spinal cord, has also been reported to reverse both thermal hyperalgesia and allodynia after SNL. In addition, selective ablation of MOR-expressing RVM neurons has been reported to prevent SNLinduced experimental hypersensitivity. However, neither DLF lesions nor microinjection of lidocaine into the RVM reduced cutaneous hypersensitivity within three days after SNL—they did so only 4-6 or more days after SNL. Based on these and similar findings, it has been proposed that physiological changes in the RVM contribute to the maintenance of neuropathic pain but not to its initiation.

Figure 10:
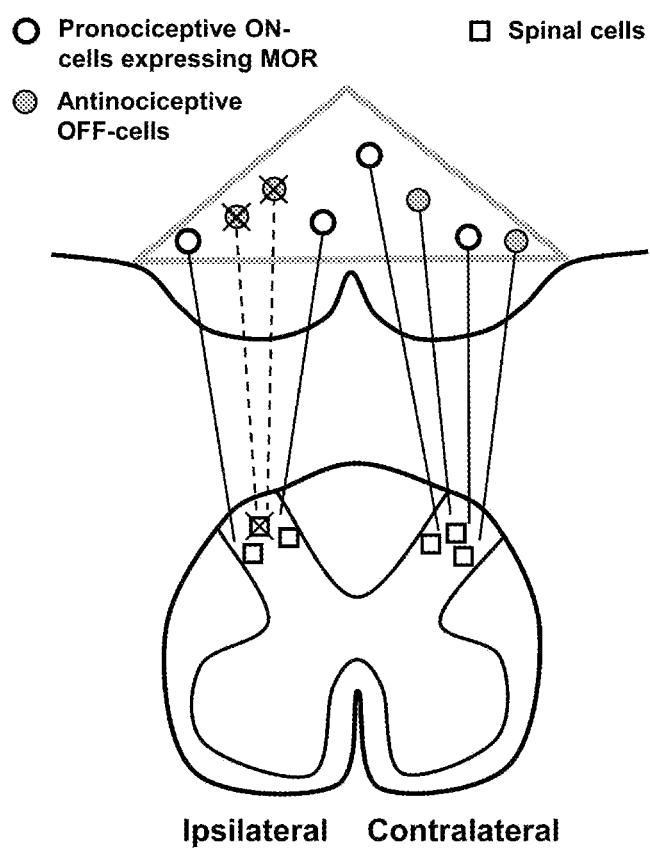
FIG. 10 depicts the proposed mechanism for the loss of descending inhibitory tone contributing to cutaneous hypersensitivity.

In one example, inventors found that the number of RVM neurons ipsilateral to SNL was significantly decreased compared to sham-operated rats. Several prior studies have shown that neurons at the spinal level undergo apoptosis ipsilateral to peripheral nerve injury and apoptosis has been reported in cortex in response to nerve injury. Apoptosis would be expected to result in cell loss, although to date the loss of neurons in those regions has been controversial. The inventors' finding of neuronal loss in the RVM suggests that death of pain modulatory neurons contributes to the pathophysiology of neuropathic pain. Although it is possible that both pro- and anti-nociceptive neurons are lost after SNL, the most parsimonious interpretation of the inventors' findings is that SNL selectively kills antinociceptive RVM neurons, thereby facilitating cutaneous hypersensitivity as shown in FIG. 10.

Figure 7:
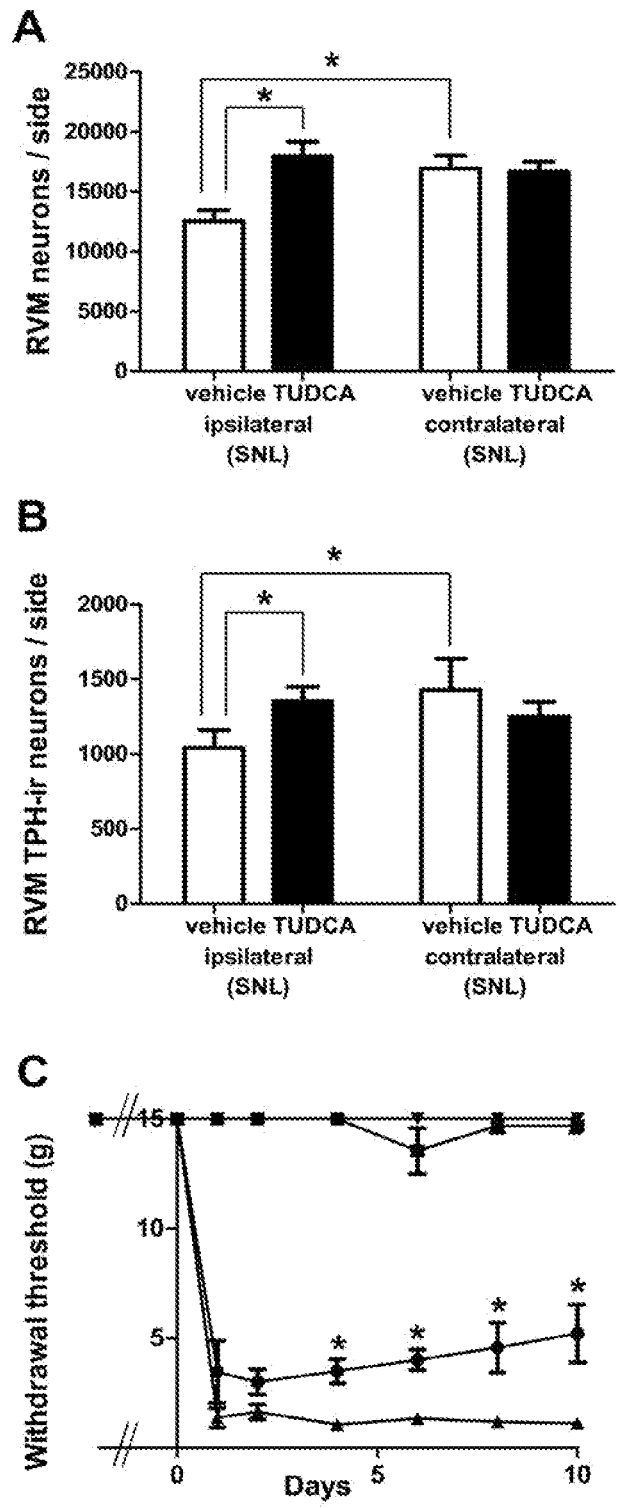
FIG. 7 shows that TUDCA prevented neuronal loss after SNL, including serotonergic cell loss, and partially reversed SNL-induced mechanical hypersensitivity as shown in panels A-C.

In another example, blocking the cell loss with TUDCA can significantly decrease tactile hypersensitivity four or more days after SNL but does not reduce hypersensitivity one-to-three days after SNL as shown in FIG. 7. Thus the inventors' findings suggest that could be efficacious in treating neuropathic pain in humans. They also suggest that cell loss underlies the RVM's contribution to the maintenance phase of neuropathic pain. Glial activation in the RVM may also contribute to cutaneous hypersensitivity, although since the inventors found that it occurs bilaterally it would not by itself explain the unilateral decrease in withdrawal thresholds; instead, glial activation may be an important factor in the initiation of neuropathic pain.

Previous work has suggested that the pathology of neuropathic pain is due in part to death of neurons in the CNS and/or dorsal root ganglia. Work by the inventors has revealed that neuropathic pain may be due in part to death of antinociceptive rostral ventromedial (RVM) neurons, leading to decreased descending inhibition of nociception. Subsequent to the cell loss, gliosis occurs, which may also play a role in neuropathic pain. The inventors have discovered that the apotosis (programmed cell death) inhibitor tauroursodeoxycholic acid (TUDCA) significantly reduced both neural loss and the increase in glia, and partially reversed spinal nerve ligation (SNL)-induced mechanical hypersensitivity. Among the RVM neurons, the inventors discovered that serotonergic (5-HT) neurons decreased significantly ipsilateral to SNL. Further, the density of 5-HT-immunoreactive varicosities in the superficial dorsal horn of the spinal cord was lowered.

In another example, the inventors also found that the number of glia increased after SNL. This increase was blocked by TUDCA, suggesting it may represent gliosis in response to RVM neuronal death. Further, the inventors found that MOR-ir appeared not to decrease after SNL and RVM neurons (including 5-HT neurons) expressing MOR were still observed after SNL.

In another example, administration of TUDCA blocks RVM cell loss. The inventors findings also indicate that the antiapoptotic activity of TUDCA attenuated the RVM cell loss.

In another example, the inventors found that TUDCA specifically block loss of RVM neurons expressing the neurotransmitter serotonin (5-HT). The 5-HT neurons that are lost appear to be neurons that inhibit nociception (i.e. pain).

Methods

Animals

Male Sprague-Dawley rats (150-250 g; Harlan, Madison, Wis.) were used for these studies; 5-10 animals were used for each experimental group. All experiments and 5 procedures were performed using protocols approved by the University of Minnesota Institutional Animal Care and Use Committee.

SNL Surgery:

Rats were divided into two experimental groups: a group in which the L5 spinal nerve was ligated and cut, and a sham-operated control group. The left L5 spinal nerve was isolated, tightly ligated and cut distal to the ligation under isoflurane anesthesia (1.5%). The surgical procedure for the sham-operated group was identical to that of the SNL group, except that the L5 spinal nerve was not ligated or cut. General behavior of the rats was monitored before and after the surgery. Any rats showing difficulty elevating a hindpaw were discarded from the study.

Drug Treatments:

Rats were treated with 5,7-dihydroxytryptamine (5,7-DHT: 100 µg/10 µl, intracisternal injection) to induce loss of RVM serotonergic neurons. Rats were randomly assigned to one of four groups for these experiments: (1) L5 SNL with 5,7-DHT; (2) L5 SNL with vehicle injection; (3) sham with 5,7-DHT; and (4) sham with vehicle. Injections were given ten days after surgery; animals receiving vehicle injections received sterile saline (10 µl, intracisternal injection). To prevent damage to noradrenergic (NE) neurons, the inventors pre-treated animals 30 minutes before 5,7-DHT and saline administration with desipramine (20 mg/kg i.p.), an inhibitor of neuronal NE reuptake. To test the effects of inhibiting apoptosis on SNL, the inventors administered a systemically active inhibitor of apoptosis, tauroursodeoxycholic acid (TUDCA) (300 mg/kg i.p. or saline prior to and after surgery. For each group, injections were given every-other day, starting 3 days prior to surgery and continuing until sacrifice. To confirm the efficacy of TUDCA, the inventors tested its effects on dexamethasone-induced apoptosis in thymus. Two TUDCA injections (300 mg/kg i.p.) were given: one to two days prior to dexamethasone (1 mg/kg i.p.) administration and one the day of dexamethasone administration. Control animals were given saline injections instead of TUDCA solution. Rats were killed one day after dexamethasone administration.

Perfusion:

Rats were deeply anesthetized with a mixture of ketamine (67.5 mg/kg), xylazine (22.5 mg/kg) and acepromazine (1 mg/kg) and perfused via the ascending aorta with 180 ml oxygenated Ca 2+-free Tyrode's solution (pH 7.2) followed by 500 ml of 4% formaldehyde (freshly made from paraformaldehyde) in 0.16 M phosphate buffer (pH 6.9). Immediately after fixation, brains were removed and stored in a 5% sucrose solution prior to sectioning.

Histology and Immunocytochemistry:

The RVM and spinal cord were sectioned using a freezing microtome (Leica, SM2400) at a nominal thickness of 50 µm. The free-floating sections were washed in phosphate-buffered saline (PBS: 0.8% (w/v) NaCl, 0.02% KCl, 0.144% Na2HPO4, 0.024% KH2PO4, pH=7.4) for three 5-minute intervals. RVM sections were incubated overnight at 4° C. in solutions containing one of the following antibodies: (1) mouse anti-TPH (T0678, Sigma, Saint Louis, Mo., 1:1000), (2) mouse anti-NeuN (MAB377, Millipore, Temecula, Calif., 1:500), (3) mouse anti-CD11b (MCA75GA, AbD Serotec, Oxford, UK, 1:1000), or (4) mouse anti-GFAP (GA5, #3670, Cell Signaling Technology, Danvers, Mass., 1:1000). Spinal cord sections were incubated with goat anti-5-HT (#20079, ImmunoStar, Hudson, Wis., 1:1000). Sections were then washed in PBS and incubated for 4 h with Cy2-conjugated donkey anti-mouse IgG or Cy3-donkey anti-goat IgG (1:500). Secondary antibodies were purchased from Jackson ImmunoResearch (West Grove, Pa.). The fluorescent Nissl stain ethidium bromide (30 nM, Sigma) was used to counterstain RVM tissue (Schmued et al., 1982). Tissue was stained for the mu-opioid receptor (MOR) after heat-induced epitope retrieval. Ten micron-thick cryostat sections were exposed to a temperature of 101° C. for 30 min in a 10 mM solution of citric acid. Tissue was then washed three times (five minutes each) in tris-buffered saline (TBS: 135 mM NaCl and 25 mM Tris-HCl;

pH=7.4) and incubated overnight at 4° C. in mouse anti-TPH and guinea pig anti-MOR. (The guinea pig anti-MOR was characterized as specific using knockout mice; (Liu et al., 2011), in press). Tissue was washed in TBS and then incubated in Cy3-conjugated donkey anti-guinea pig IgG, Cy5-conjugated donkey anti-mouse IgG and the nucleic acid stain, SYBR Green II (S-7564, Invitrogen, Carlsbad, Calif., 1:10,000) for 2 h. 8

All tissue was dehydrated in graded alcohols (50-100%) and cleared in xylene. The slides were mounted with coverslips using DPX (Fluka, Ronkonkoma, N.Y.).

Figure 1:
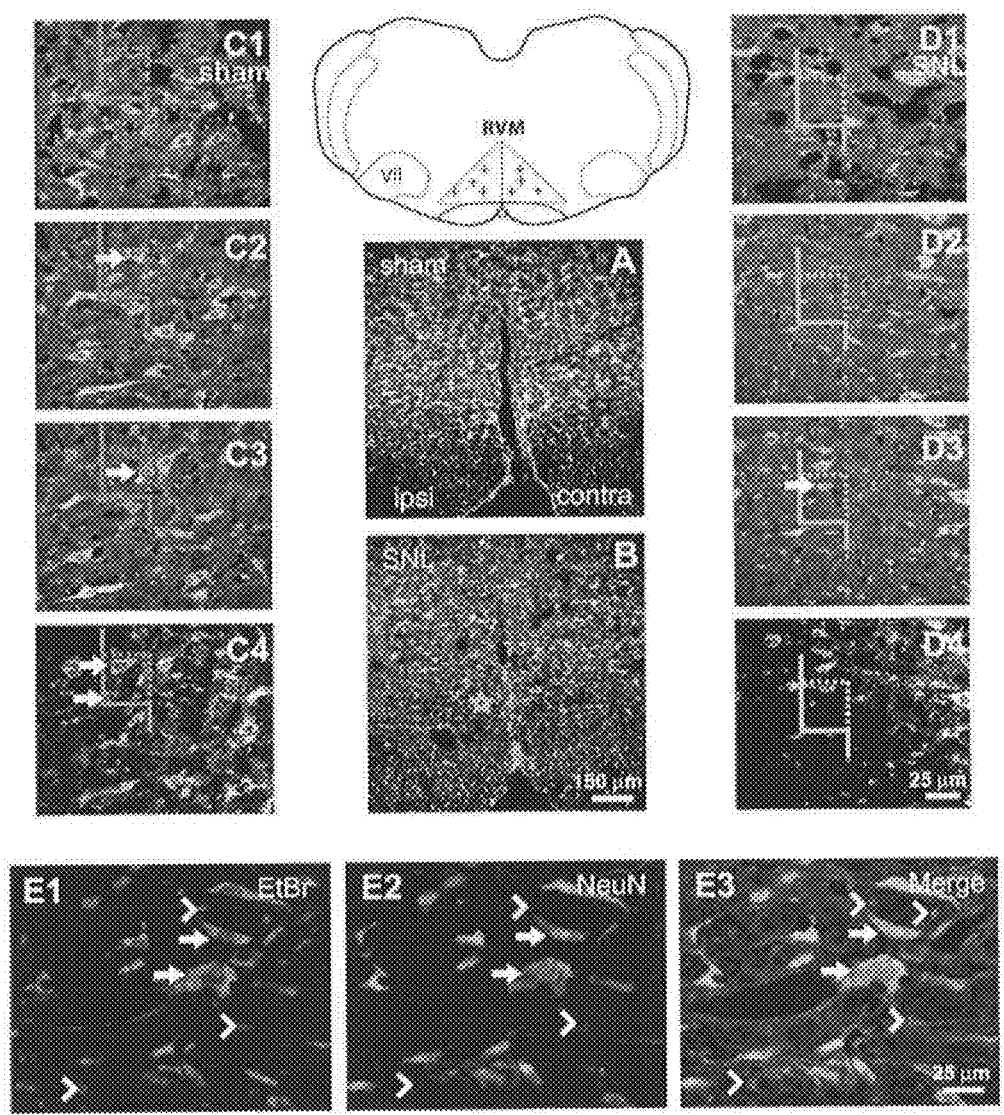
FIG. 1 depicts the definition of RVM and description of cell-counting methods as shown in panels A, B, C1-4, D1-4 and E1-3.
Figure 2:
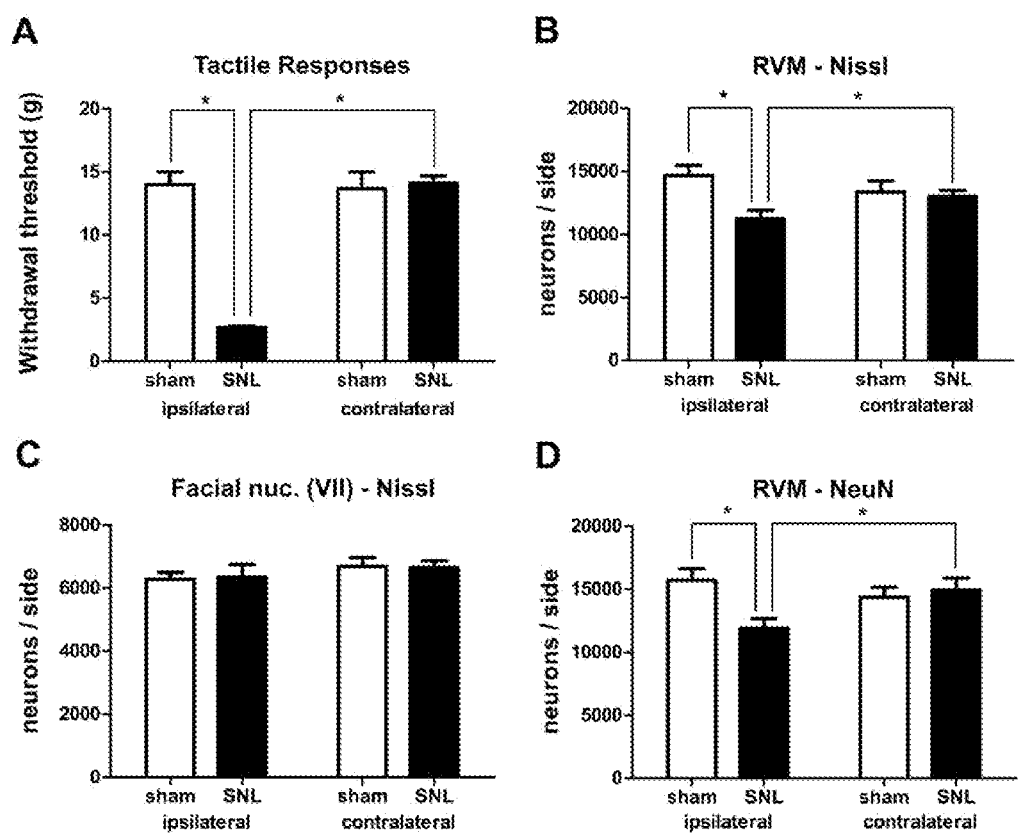
FIG. 2 depicts SNL-induced tactile hypersensitivity and neuronal loss in RVM as shown in panels A-D.
Figure 3:
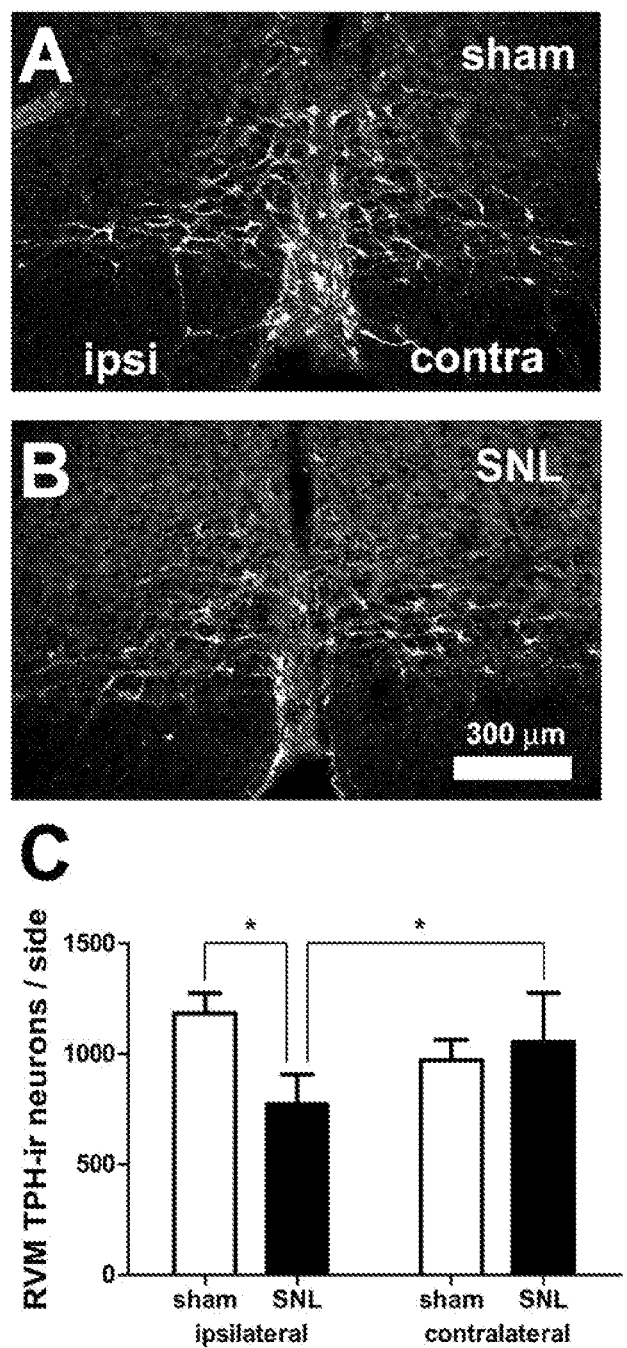
FIG. 3 depicts SNL-induced loss of tryptophan hydroxylase-immunoreactive (TPH-ir) neurons, which synthesize serotonin (5-HT) in the RVM as shown in panels A-C.
Figure 4:
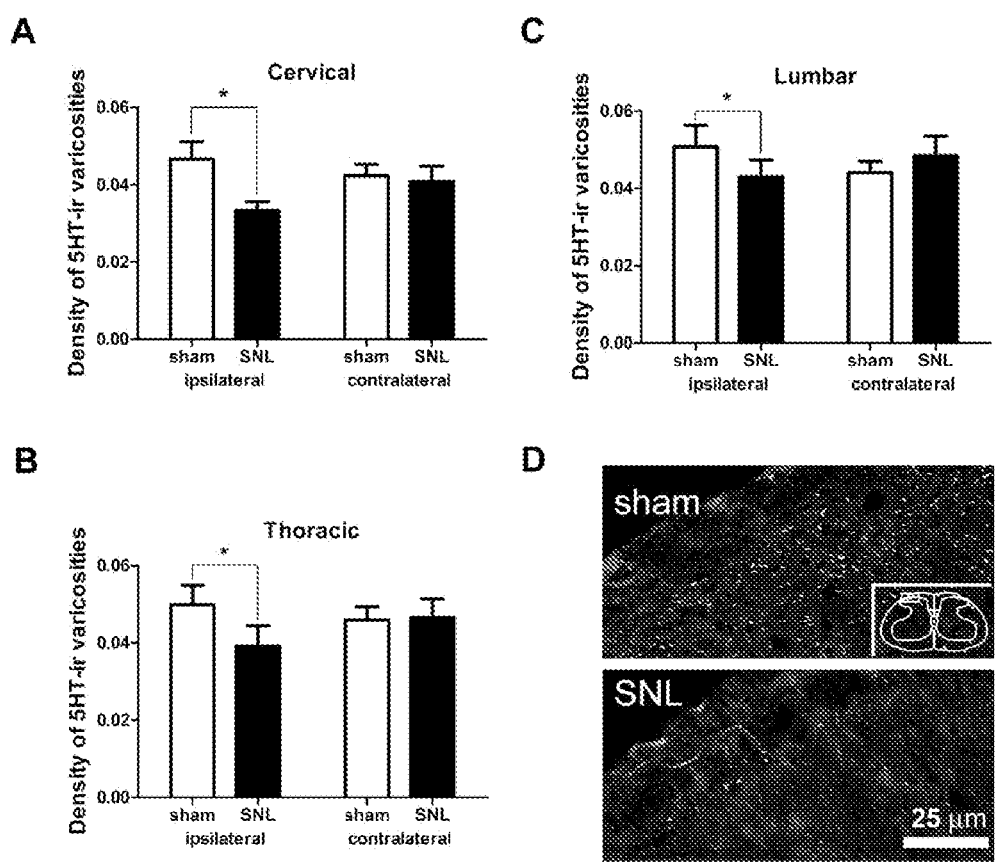
FIG. 4 depicts the effect of SNL on serotonin-immunoreactive (5-HT-ir) nerve varicosities in the superficial dorsal horn of the spinal cord as shown in panels A-D.
Figure 5:
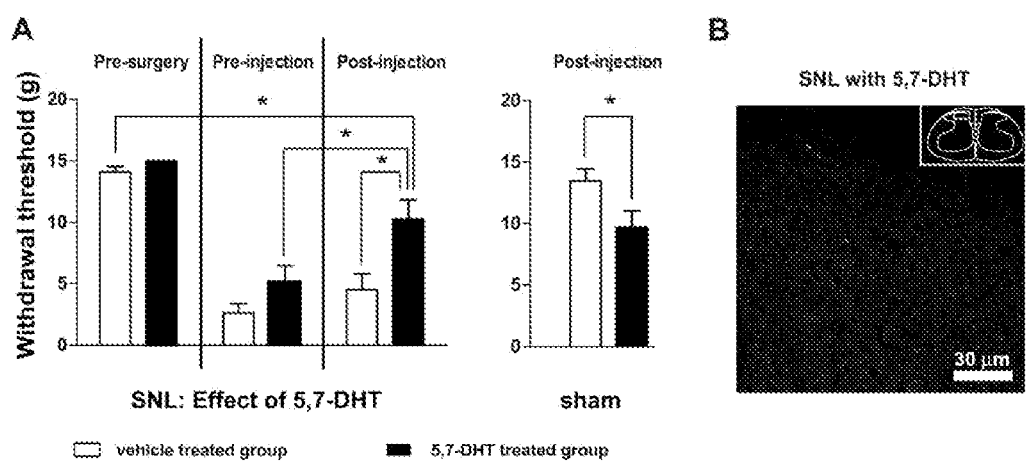
FIG. 5 depicts that intracisternal injection of the serotonin neurotoxin 5,7 dihydroxytryptamine (5,7-DHT) partially reversed mechanical hypersensitivity after SNL as shown in panels A and B.

Microscopy and Quantification:

Conventional microscopy was used to collect images of the RVM for cell counting. An Olympus BX50 fluorescence microscope (Tokyo, Japan) equipped with filter sets designed to allow selective visualization of Cy2 and Cy3 was used. Microscopic images were collected with a Scion 1346 digital camera. Confocal images were collected using an Olympus FluoView FV1000 microscope (Tokyo, Japan). ImageJ 1.29 (developed at NIH and available at http://rsb.info.nih.gov/ij/) or Photoshop were used to adjust contrast and brightness in images. The RVM was defined as an isosceles triangle that lies at the level of the facial nucleus with a base having a width equal to that of the combined pyramidal tracts, and its height equal to half the width of the base as shown in FIG. 1. The RVM extended from the rostral end of inferior olive to the caudal end of the trapezoid body. It was divided into ipsilateral and contralateral sides by the midline. In Nissl-stained sections of the RVM, two distinct populations of cells were found: (1) cells with dark cytoplasm, a vacuous nucleus and a single distinct nucleolus as shown in FIG. 1E1, arrows, and (2) cells with very lightly-stained cytoplasm, a dark nucleus, and nuclear granulations rather than a nucleolus as shown in FIG. 1E1, arrowheads. The first group was classified as neurons and the second as glia. These distinct Nissl-stained populations were confirmed by immunohistochemistry (e.g., NeuN for neurons and GFAP and CD11B for astrocytes and microglia, respectively). Cell counting was based on cells' Nissl staining (including counting of TPH-immunoreactive (-ir) neurons, which were Nissl counter-stained), except when counting NeuN-labeled cells (see below). The numbers of cells were estimated separately for each half of the RVM (i.e. both ipsilateral and contralateral to the surgery). Systematic random sampling and unbiased stereological methods were used for quantification as described previously. Five RVM sections (each 50 μm thick) per animal were sampled; the first section sampled was selected randomly. The sampling interval thereafter was determined based on the number of sections within the RVM and was usually every sixth section. For each selected section, a low-magnification (2×) image of the RVM was captured. A grid was randomly cast over the image as shown in FIG. 1, line drawing, and systematic random sampling was again used when choosing the grid intersections to be evaluated. Once an intersection was chosen, a stack of images was made at 40× while focusing through the full thickness of the section as shown in FIG. 1, C-D. Cells were counted as follows. A counting frame was superimposed on the stack of images. The right boundary and the upper boundary of the counting frame were used as acceptance lines as shown in FIG. 1, C-D, dotted lines; the other two boundaries were forbidden lines as shown in FIG. 1, C-D, solid lines. Neurons were counted only if nuclei (for NeuN-labeled neurons) or nucleoli (for Nissl-stained neurons) either fell entirely inside the counting frame or if they crossed an acceptance line without also crossing a forbidden line. NeuN-labeled neurons were counted when the top of the nucleus was found within the thickness of the tissue section. Nissl-stained neurons were counted when the nucleolus was present within the thickness of the tissue section and TPH-ir neurons were counted based on their Nissl counterstaining. To estimate the total number of neurons (N) in the RVM per animal, the inventors used the following equation:

$$N = D \times V$$

where D=the neuronal density of the RVM, V=the volume of the RVM. To estimate the neuronal density of the RVM in each rat, the inventors used the following equation:

$$D = N(a \times t \times g)$$

where N=the number of neurons counted per rat, a=2,500 μm2 (the area of the counting frame sampled), t=50 μm (the thickness of the section sampled), and g=20 (the number of counting frames sampled per rat). To estimate the volume of the RVM from each rat, the inventors used the following equation:

$$V = \Sigma(A \times I \times t)$$

where A=the cross sectional area of RVM in which the sections were sampled, I=the interval between adjacent sampled sections, and t=50 μm (the thickness of section sampled). To determine the effects of SNL on spinal 5-HT innervation, the density of 5-HT labeling was examined in the superficial dorsal horn using a 40×/1.4 NA objective. The number of 5-HT varicosities in the lateral and medial superficial dorsal horn was determined using the "Finding Maxima" routine of ImageJ. The density was then calculated by dividing those numbers by the corresponding cross-sectional areas of the regions being examined. The same value for noise tolerance was used in all cases.

Statistics:

Unless otherwise noted, differences among treatment groups were identified by 2-way analyses of variance (ANOVA); post-hoc comparisons were made with a Bonferroni test. However, chi-square tests were used to detect differences in proportions. $P<0.05$ was considered significant. Statistical tests were performed using the GraphPad Prism software (La Jolla, Calif.) and the statistical tools available on the GraphPad website (http://wwwgraphpad.com).

Von Frey Testing for Tactile Hypersensitivity:

Mechanical sensitivity was determined by measuring the paw withdrawal threshold in response to the application of von Frey filaments, using the up-down method of Chaplan. In brief, rats were placed on a wire mesh surface, covered by an inverted plastic cage and allowed to habituate for 15 min. Filaments were then applied to the plantar surface of the hindpaw. If application of the filament evoked no response, the next-larger filament was applied; if application elicited withdrawal, the next-smaller filament was applied. This sequence was repeated until the largest filament was used or until four filaments were applied after the first withdrawal was noted. Withdrawal thresholds were measured prior to surgery and at 2-3 day intervals after surgery. In all cases, thresholds were measured bilaterally.

Results

Figure 6:
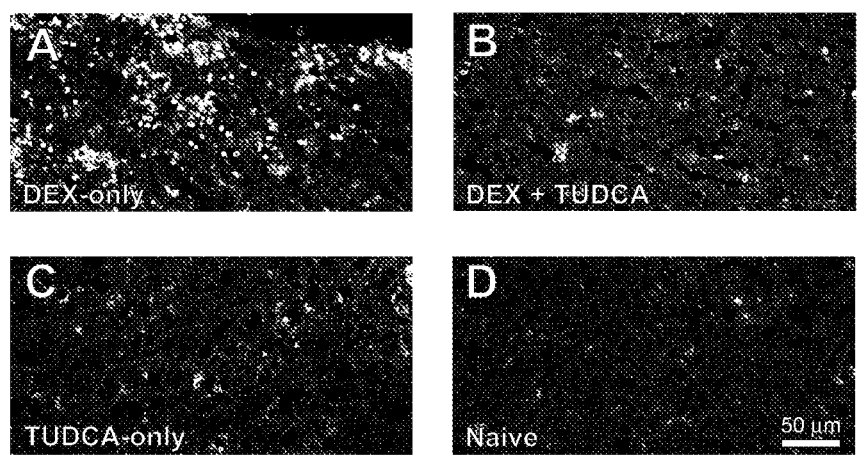
FIG. 6 shows that TUDCA inhibited dexamethasone-induced apoptosis in thymus as shown in panels A-D.

Administration of an Apoptosis Inhibitor Reduced Both the Loss of RVM Neurons and Cutaneous Hypersensitivity after SNL Previous studies have reported neuronal apoptosis in the spinal cord and cerebral cortex after nerve injury. To test whether RVM cell loss was due to apoptosis, the inventors gave rats a long-acting inhibitor of apoptosis that can be administered systemically. Ursodeoxycholic acid (UDCA) is a bile acid used for treating hepatic disease that has been shown to inhibit apoptosis and acts at least in part by inhibiting the translocation of Bax from the cytosol to the mitochondrion. Because of its greater solubility in water, in these experiments the inventors administered the taurine conjugate of UDCA (TUDCA), which similarly inhibits apoptosis and promotes cell survival. The inventors first confirmed the actions of TUDCA by testing its effects on apoptosis in the thymus. The inventors induced apoptosis in the thymus by treatment with 1 mg/kg dexamethasone, an immunosuppressant glucocorticoid, which greatly enhanced staining for caspase-3. However, in rats treated with both TUDCA and dexamethasone, the inventors found a marked decrease in caspase-3 labeling compared to treatment with dexamethasone alone as shown in FIG. 6.

In the brain stem, the inventors found that administration of TUDCA prevented loss of RVM neurons after SNL as shown in FIG. 7. In rats receiving SNL and treated with TUDCA, the number of RVM neurons ipsilateral to the lesion was 17,976±1,202, which was significantly higher (by 43%) than the number found in the ipsilateral sides of vehicle-treated rats that had received SNL (12,540±930; $p<0.05$, n=8 in each group, d.f.=14, FIG. 7A). As expected, in vehicle-treated rats, the number of RVM neurons in the ipsilateral side (12,540±929) was significantly less (by 26%) than the number found in the contralateral side (16,949±1,074, $p<0.05$, FIG. 7A). There was no significant difference between the number of neurons in the ipsilateral and contralateral sides of TUDCA-treated rats receiving SNL (TUDCA ipsi: 17,976±1,202, TUDCA contra: 16,675±828, FIG. 7A), nor between the numbers of neurons found in the contralateral sides of the two treatment groups (SNL with TUDCA: 16,675±828, SNL with saline: 16,949±1,074, $p>0.05$, FIG. 7A). TUDCA also prevented the loss of 5-HT neurons in the RVM. The number of RVM 5-HT neurons ipsilateral to SNL in TUDCA-treated animals (1,353±96) was significantly higher (by 30%) than the number in vehicle-treated rats (1,043±118, $p<0.05$, n=8 in each group, d.f.=14, FIG. 7B). Again, as expected, the number of 5-HT-ir RVM neurons in the ipsilateral side of vehicle-treated rats (1,043±118) was significantly less (by 27%) than that in the contralateral side (1,427±211, $p<0.05$, FIG. 7B). In TUDCA-treated rats receiving SNL, there was no significant difference between the number of neurons in the ipsilateral and contralateral sides (TUDCA ipsi: 1,353±96, TUDCA contra: 1,251±99, $p>0.05$, FIG. 7B). TUDCA administration also reduced SNL-induced mechanical hypersensitivity.

Beginning at day 4 post-SNL, the withdrawal thresholds of the ipsilateral hindpaws of TUDCA-treated rats (Day 4: 3.5±0.5 g; Day 6: 4.0±0.5 g; Day 8: 4.6±1.1 g; Day 10: 5.2±1.3 g) were significantly higher than those animals treated with vehicle (Day 4: 1.1±0.3 g; Day 6: 1.3±0.2 g; Day 8: 1.2±0.3 g; Day 10: 1.2±0.2 g; $p<0.05$, n=10 TUDCA, n=9 vehicle, d.f.=119, FIG. 7C). Despite the efficacy of TUDCA, though, the inventors found neither caspase-3 labeling, caspase-6 labeling nor terminal deoxynucleotidyl transferase-mediated dUTP-biotin nick-end labeling (TUNEL) in the RVM after SNL.

Glia: Activation and Increased Numbers After SNL

Figure 8:
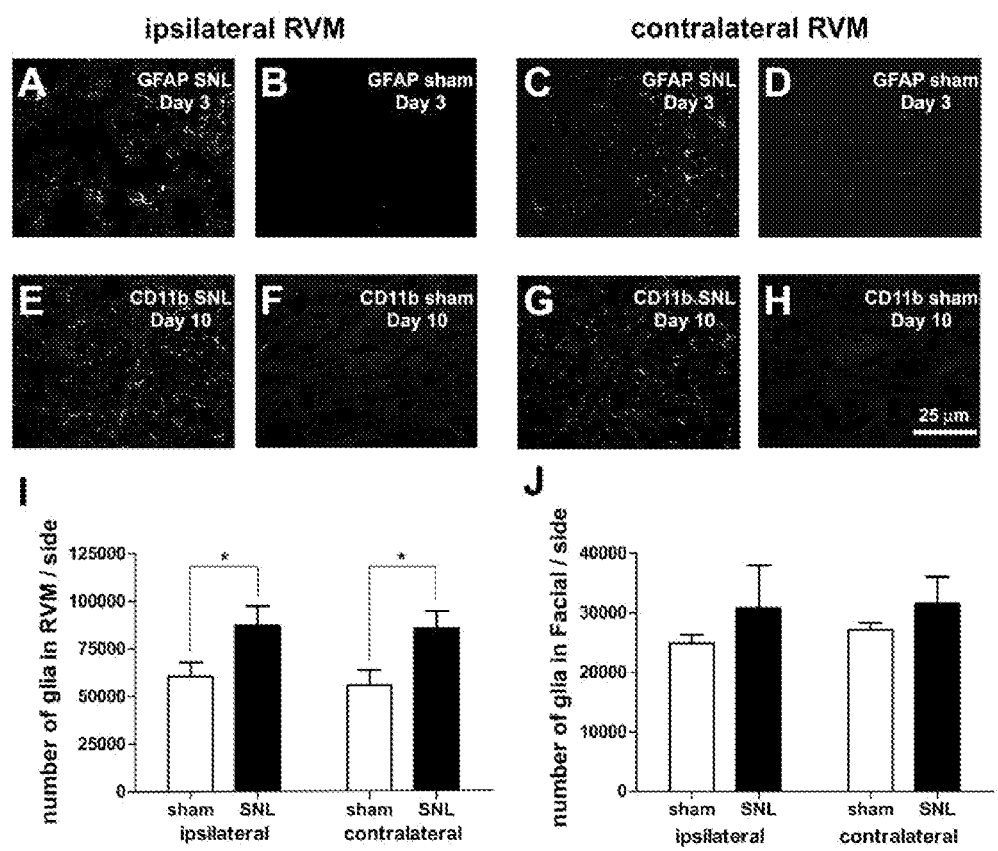
FIG. 8 shows that SNL induced a bilateral activation of astrocytes and microglia and an increase in glial number as shown in panels A-J.

RVM glial activation appears to have a role in descending facilitation of nociception in a model of persistent pain. To determine whether glial activation might be responsible for the neuronal loss, the inventors stained for markers of astrocytes (GFAP) and microglia (CD11B) in RVM after SNL. At day three, the inventors found a bilateral increase in activation of astrocytes in animals receiving SNL as compared to sham-operated animals as shown in FIG. 8A-D; GFAP staining was decreased by day 10. Conversely, although little labeling was observed at day three, the inventors found markedly stronger labeling for CD11B at day 10 in rats receiving SNL. Again, the labeling increased both ipsilateral and contralateral to SNL as shown in FIG. 8E-H. Using Nissl-stained tissue, the inventors also found a significant bilateral increase in numbers of glia in the RVM of SNL-treated animals as compared to sham-operated animals (SNL ipsi: 87,277±10,354 vs. sham ipsi: 60,430±7,551 or 44% higher, SNL contra: 85,903±9,091 vs. sham contra: 56,104±7,912 or 52% higher; $p<0.05$, n=5 in each group, d.f.=8, FIG. 8I). To determine whether this increase in glial activation and number was specific to the RVM, the inventors examined the adjacent facial nucleus. In that nucleus the inventors found no significant increase in the number Nissl-stained glia as shown in FIG. 8J or in the activation of glia in SNL-treated rats, compared to sham-operated rats. Treatment with TUDCA significantly reduced the increase in RVM glia observed after SNL (TUDCA ipsi: 62,306±3,736 vs. vehicle ipsi: 85,541±2,972, or 27% fewer; TUDCA contra: 60,437±4,315 vs. vehicle contra: 80,086±2,899, or 25% fewer; $p<0.05$ in both cases, n=7 TUDCA, n=6 vehicle, d.f.=11), suggesting that the increase in glia was in response to cell death.

MOR Expression in RVM After SNL

Figure 9:
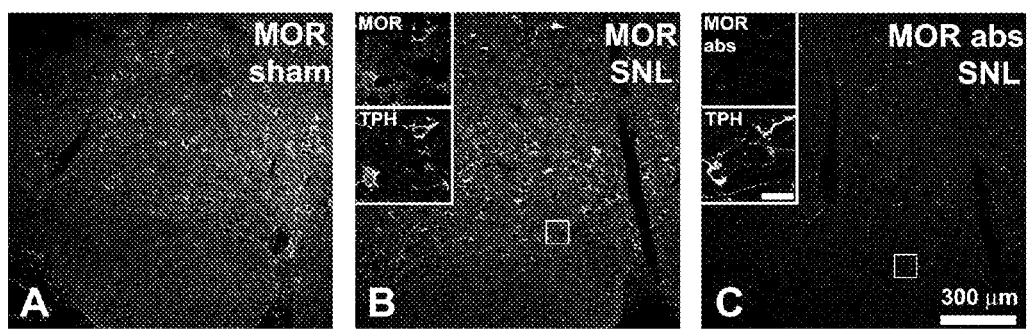
FIG. 9 shows that MOR-immunoreactivity in the RVM appears to be unchanged after SNL as shown in panels A-C.

Previous studies have suggested that RVM neurons expressing the mu-opioid receptor (MOR) mediate descending facilitation of nociception after SNL. Although RVM neurons were lost after SNL (see above), the inventors found that MOR-ir in the RVM appeared to be unchanged as shown in FIG. 9A,B. When the intensity of MOR staining was measured there was no significant difference between sham animals (55.5±2.6) and animals receiving SNL (53.7±3.2) (n=3 animals in each group, t-test, d.f.=4, $p>0.05$). The inventors also observed MOR-ir after SNL in TPH-ir neurons as well as in neurons that were not immunoreactive for TPH as shown in FIG. 9B.

Although the present invention has been described with reference to preferred embodiments, workers skilled in the art will recognize that changes may be made in form and detail without departing from the spirit and scope of the invention.

What is claimed is:

1. A method of reducing or abolishing neuropathic pain in an animal, the method comprising administering an effective amount of a tauroursodeoxycholic acid to a nerve tissue of the animal.

2. The method of claim 1, wherein the nerve tissue comprises neurons, spinal cord, and/or brain tissue.

3. The method of claim 2, wherein the neurons comprise antinociceptive neurons of a rostral ventromedial medulla.

4. The method of claim 1, wherein the tauroursodeoxycholic acid is administered in one or more ways such as orally, intravenously, and/or intramuscularly.

5. The method of claim 1, wherein the tauroursodeoxycholic acid is administered prior to and after a surgery that isolates the spinal nerve.

6. The method of claim 1, further comprising administering an effective amount of a dexamethasone in combination with the tauroursodeoxycholic acid.

7. The method of claim 1, further comprising performing a spinal nerve ligation on the animal.

8. The method of claim 1, further comprising applying von Frey filaments to the animal to measure a neuropathic pain threshold of the animal.

* * * * *

UNITED STATES PATENT AND TRADEMARK OFFICE
CERTIFICATE OF CORRECTION

PATENT NO. : 9,632,075 B2  
APPLICATION NO. : 14/355759  
DATED : April 25, 2017  
INVENTOR(S) : Leong et al.

Page 1 of 1

It is certified that error appears in the above-identified patent and that said Letters Patent is hereby corrected as shown below:

On the Title Page

In Item (73), in "Assignee", in Column 1, Line 1, delete "Meselex," and insert --Metselex,-- therefor Signed and Sealed this  
Tenth Day of April, 2018

Andrei Iancu  
*Director of the United States Patent and Trademark Office*